United States Patent
Wang et al.

(10) Patent No.: US 9,421,533 B2
(45) Date of Patent: Aug. 23, 2016

(54) CATALYST OR SYNTHESIZING 1-HEXENE FROM ETHYLENE TRIMERIZATION AND APPLICATION THEREOF

(75) Inventors: Gang Wang, Daqing (CN); Sihan Wang, Daqing (CN); Zhonghua Yang, Daqing (CN); Jiabo Qu, Daqing (CN); Baojun Zhang, Daqing (CN); Qian Chen, Daqing (CN); Deshun Zhang, Daqing (CN); Libo Wang, Daqing (CN); Yali Wang, Daqing (CN); Buwei Yu, Daqing (CN); Xiuhui Wang, Daqing (CN); Fuling Huang, Daqing (CN); Xuemei Han, Daqing (CN); Dongmei Niu, Daqing (CN); Shukun Sun, Daqing (CN); Wenchao Zhang, Daqing (CN); Hua Li, Daqing (CN); Gongchen Yan, Daqing (CN)

(73) Assignee: PETROCHINA COMPANY LIMITED, Dongcheng (CN)

( * ) Notice: Subject to any disclaimer, the term of this patent is extended or adjusted under 35 U.S.C. 154(b) by 818 days.

(21) Appl. No.: 13/519,791

(22) PCT Filed: Jul. 22, 2010

(86) PCT No.: PCT/CN2010/001111
§ 371 (c)(1),
(2), (4) Date: Aug. 14, 2012

(87) PCT Pub. No.: WO2011/079493
PCT Pub. Date: Jul. 7, 2011

(65) Prior Publication Data
US 2012/0310025 A1    Dec. 6, 2012

(30) Foreign Application Priority Data
Dec. 29, 2009  (CN) .......................... 2009 1 0243233

(51) Int. Cl.
*C07C 2/32* (2006.01)
*B01J 31/12* (2006.01)
*B01J 31/18* (2006.01)
*B01J 31/14* (2006.01)
*B01J 31/16* (2006.01)

(52) U.S. Cl.
CPC .............. *B01J 31/188* (2013.01); *B01J 31/143* (2013.01); *B01J 31/1616* (2013.01); *C07C 2/32* (2013.01); *B01J 2231/20* (2013.01); *B01J 2531/007* (2013.01); *B01J 2531/62* (2013.01); *C07C 2521/08* (2013.01); *C07C 2531/14* (2013.01); *C07C 2531/24* (2013.01); *Y02P 20/52* (2015.11)

(58) Field of Classification Search
CPC combination set(s) only.
See application file for complete search history.

(56) References Cited

U.S. PATENT DOCUMENTS

| | | | |
|---|---|---|---|
| 5,910,619 A | 6/1999 | Urata et al. | |
| 7,511,183 B2 * | 3/2009 | Blann et al. | ................... 585/513 |
| 7,786,336 B2 * | 8/2010 | Zhang | .................. B01J 31/0201 502/103 |
| 8,227,653 B2 * | 7/2012 | Weber | ....................... C07C 2/30 526/75 |
| 2007/0299290 A1 * | 12/2007 | De Boer et al. | ............... 585/513 |

FOREIGN PATENT DOCUMENTS

| | | | |
|---|---|---|---|
| CN | 1872416 A | * | 12/2006 |
| EP | 0608447 A1 | | 8/1994 |
| EP | 0699648 A1 | | 3/1996 |
| WO | 2004005647 A1 | | 1/2004 |

OTHER PUBLICATIONS

T. Monoi and Y. Sasaki. "Silica-supported Cr[N(SiMe3)2]3/isobutylalumoxane catalyst for selective ethylene trimerization". Journal of Molecular Catalysis A: Chemical, 187 (2002), 135-141).*
Grand and Wilkie, "Fire Retardancy of Polymeric Materials", Copyright 2000, p. 357, 360 and 367.*

* cited by examiner

*Primary Examiner* — In Suk Bullock
*Assistant Examiner* — Ali Z Fadhel
(74) *Attorney, Agent, or Firm* — Benjamin Aaron Adler

(57) ABSTRACT

A catalyst for synthesizing 1-hexene from ethylene trimerization and its application are provided. Said catalyst consists of (a) the compound containing P and N, (b) electron donor, (c) Cr compound, (d) carrier and (e) accelerator. The molar ratio of (a), (b), (c), (d) and (e) is 0.5-100:0.5-100:1:0.5-10:50-5000. The catalyst is prepared by mixing the components of (a)-(e) in an ethylene trimerization apparatus in situ and ethylene is introduced into the apparatus continuously. The prepared catalyst can be used to synthesize 1-hexene from ethylene trimerization in the inert solvents. The trimerization is performed at 30-150° C. and 0.5-10.0 MPa for 0.1-4 hours. The catalyst has high catalytic activity and high 1-hexene selectivity. During the process of ethylene trimerization, by-product polyethylene does not stick to the apparatus.

12 Claims, No Drawings

CATALYST OR SYNTHESIZING 1-HEXENE FROM ETHYLENE TRIMERIZATION AND APPLICATION THEREOF

FIELD OF THE INVENTION

The present invention relates to a catalyst for synthesizing 1-hexene from ethylene trimerization and application thereof.

BACKGROUND OF THE INVENTION

EP 699648 discloses a Cr-based catalyst, which comprises a chromic salt A, an organic aluminide B, a pyrrole compound C and a 13(IIIB) chloride or 14(VIB) chloride. The best chromic salts include chromium 2-ethylhexanoate, chromium naphthenate and chromium acetylacetone. A, B and D have effect on the catalytic activity, and C influences the selectivity of 1-hexene. The selectivity of 1-hexene is 80%, and the purity is 98-99%. The advantages are that 1-hexene is used as solvent for catalyst preparation and ethylene trimerization, thus the apparatus for separation of solvent with 1-hexene and cost thereof are omitted.

EP 0608447A discloses a Cr-based catalyst composition as the catalyst for ethylene oligomerization and/or copolymerization, in which the catalyst composition contains a Cr-containing compound, a pyrrole compound, a Lewis acid and/or metal alkyl compound as an activator, and optionally a halogen source which can be either inorganic halides or various organic halides. The catalyst has high 1-hexene selectivity, but with low catalytic activity.

JP 0832519 discloses $Sn(OSO_2F_3)_2$ compound is used in place of halogen source as mentioned above in EP 0608447A, thus to form a new quaternary Cr-based catalyst composition. The activity and selectivity of this composition have not been improved significantly.

U.S. Pat. No. 5,910,619 discloses 1,2,3,4,5,6-hexachlorocyclohexane is used as improver to form a quaternary catalyst composition, the catalytic activity of which is improved slightly. CN 1294109A (the title of which is a catalyst for preparing 1-hexene from ethylene oligomerization and application thereof) discloses a new catalyst system, the catalytic activity of which is improved greatly. However, these catalysts cannot meet current requirements yet. There is still a need for improving the property of catalyst so as to increase catalytic activity.

In the ethylene oligomerization as disclosed in WO2004/05647, the content of 1-octylene is at most 69.3%, and the content of 1-hexene is 10-20%.

SUMMARY OF THE INVENTION

The aim of the present application is to develop a catalyst containing (a) the compound containing P and N, (b) electron donor, (c) Cr compound, (d) carrier and (e) accelerator. This catalyst is used for preparing 1-hexene from ethylene trimerization. Cr compound can form three unoccupied orbitals under the effect of ligand and accelerator, which may facilitate the coordination of ethylene molecular, and then β-H elimination reaction occurs to obtain 1-hexene. And the by-product polyethylene is more easily formed on the carrier $SiO_2$ so as to avoid sticking to the apparatus and facilitate long periodic run of reactor.

The present application is directed to a Cr catalyst system used for ethylene trimerization, which is the composition containing the following:

(1) compound (a) containing P and N, with formula:

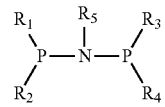

wherein $R_1$, $R_2$, $R_3$ and $R_4$ independently are selected from the group consisting of phenyl, benzyl and naphthyl, $R_5$ is selected from the group consisting of isopropyl, butyl, cyclopropyl, cyclopentyl, cyclohexyl and fluorenyl;

(2) electron donor (b), which is 1,4-dichlorobenzene, 1,1,2-trichloroethane, 1,2-dichlorethane, chlorobenzene, 1,2-dichlorobenzene, 1,3-dichlorobenzene and/or 1,4-dichlorobenzene;

(3) Cr compound (c), which is chromium isooctoate, chromium chloride tetrahydrofuran and/or chromium acetylacetonate;

(4) carrier (d), which is $SiO_2$; and (5) accelerator (e), which is trimethyl aluminium, triethyl aluminium, tripropyl aluminium, tributyl aluminium and/or triisobutyl aluminium.

The molar ratio of (a), (b), (c), (d) and (e) is 0.5-100:0.5-100:1:0.5-10:50-5000, preferably 1-80:1-70:1:1-8:100-4000.

The five components (a)-(e) can be mixed under inert atmosphere for 10 minutes, then added to reactor, with ethylene introduced to undergo trimerization. Alternatively, the five components (a)-(e) can be directly added to reactor, with ethylene introduced to undergo trimerization. The reaction is usually at the temperature of 30-150° C., preferably of 20-90° C., under the pressure of 0.5-10.0 MPa, preferably of 1-10 MPa, more preferably of 2-6 MPa for 0.1-4 hours, preferably 0.3-1 hours, more preferably 0.5-0.7 hours.

The ethylene trimerization is mainly carried out in an inert solvent. The optional solvents include alkane, aromatic hydrocarbon, halohydrocarbon and alkene and so on. The typical solvents include, but not limited to, benzene, toluene, xylene, isopropylbenzene, n-heptane, n-hexane, methyl cyclohexane, cyclohexane, 1-hexene, 1-octylene and ionic liquids.

The catalyst has high catalytic activity and high 1-hexene selectivity. What is more, by-product polyethylene does not stick to the apparatus.

DETAILED DESCRIPTION OF THE INVENTION

The following examples are only intended to illustrate the present application without limiting the scope of the present application.

Example 1

1. Preparation of (diphenyl)phosphonitryl(cyclopropyl)phosphine(diphenyl) ligand (1) Preparation of N,N-diisopropyldichlorophosphoamide To a 250 ml reactor with $N_2$ sufficient exchange, the dehydrated toluene (100 ml), and $PCl_3$ (21.87 ml, 0.25 mol) are added under stirring. Then the temperature is reduced to −20° C. At room temperature, diisopropylamine (70 ml, 0.5 mol) is added slowly under stirring. After stirring for 3 hours, the temperature is raised to room temperature and then the reaction is continued for 2 hours. 38.1 g (0.19 mol, 74%) product is finally obtained after filtrating and drying.

(2) Preparation of Grignard Reagent Phenylmagnesium Bromide

To a 250 ml reactor with $N_2$ sufficient exchange, the dehydrated THF (100 ml), and magnesium powder (9.11 g, 0.375 mol) are added under stirring. The temperature is reduced by ice bath and brombenzene (11.775 g, 0.075 mol) is added dropwise slowly. Two hours later, under heating and refluxing, the reaction is continued for 2 hours. Then Grignard reagent is obtained.

(3) Preparation of Diphenyl Phosphorus Chloride

To a 250 ml reactor with $N_2$ sufficient exchange, the dehydrated THF (100 ml) is added under stirring. The temperature is reduced to 0° C. N,N-diisopropyldichlorophosphoamide (6.64 ml, 36 mmol) is added slowly. The temperature is raised to room temperature for 12 hours. Then the reaction mixture is diluted with cyclohexane and bubbled with dry H333331 gas for 1 hour. The diphenyl phosphorus chloride is finally obtained after filtrating and drying.

(4) Preparation of (diphenyl)phosphonitryl(cyclopropyl)phosphine(diphenyl)

To a 100 ml reactor with $N_2$ sufficient exchange, the dehydrated dichlormethane (20 ml), triethylamine (3.75 ml) and diphenyl phosphorus chloride (1.326 ml, 7.2 mmol) are added under stirring. The temperature is reduced to 0° C. The cyclopropylamine (3.6 mmol) is added slowly. The reaction is carried out under stirring for 30 minutes and then raised to room temperature to continue for 12 hours. The product (0.87 g, 56.6%) is finally obtained after filtrating and drying.

2. Preparation of Catalyst

To a 100 ml reactor with $N_2$ sufficient exchange, the dehydrated toluene (10 ml), (diphenyl)phosphonitryl(cyclopropyl)phosphine(diphenyl) (29 mg), triethylaluminium (10 ml), chromium isooctoate (0.03 mmol), 1,1,2,2-tetrachloroethane (7 ml, 0.54 mmol) and $SiO_2$ (0.03 mmol) are added. The reaction is undergone at room temperature for 10 minutes to obtain the catalyst for use.

3. Ethylene Trimerization 500 ml autoclave is heated and vacuumed for 2 hours. After $N_2$ exchange for several times, ethylene is introduced therein. The temperature is reduced to predetermined temperature. The dehydrated toluene (200 ml) and the catalyst as obtained above are added. Oligomerization is carried out at 90° C. under the pressure of 4.0 MPa. After 40 minutes, the temperature is reduced by ice bath, the pressure is relieved, and the reaction is terminated by 10 wt % acidified alcohol. The results are listed in appended Table 1.

Example 2

1. Preparation of (diphenyl)phosphonitryl(cyclopentyl)phosphine(diphenyl) ligand (1) Preparation of N,N-diisopropyldichlorophosphoamide
The process is the same as that in Example 1.
(2) Preparation of Grignard Reagent Phenylmagnesium Bromide
The process is the same as that in Example 1.
(3) Preparation of Diphenyl Phosphorus Chloride
The process is the same as that in Example 1.

(4) Preparation of (diphenyl)phosphonitryl(cyclopentyl)phosphine(diphenyl)

To a 100 ml reactor with $N_2$ sufficient exchange, the dehydrated dichlormethane (20 ml), triethylamine (3.75 ml) and diphenyl phosphorus chloride (1.326 ml, 7.2 mmol) are added under stirring. The temperature is reduced to 0° C. The cyclopentylamine (0.415 ml, 3.5 mmol) is added slowly. The reaction is carried out under stirring for 30 minutes and then raised to room temperature to continue for 12 hours. The product (0.55 g, 32.68%) is finally obtained after filtrating and drying.

2. Preparation of Catalyst

To a 100 ml reactor with $N_2$ sufficient exchange, the dehydrated cyclohexane (10 ml), trimethylaluminium (10 ml), (diphenyl)phosphonitryl(cyclopentyl)phosphine(diphenyl) (31 mg), $CrCl_3.(THF)_3$ (12 mg), $SiO_2$ (0.3 mmol) and 1,1,2,2-tetrabromoethane (0.02, 0.069 mmol) are added. The reaction is undergone at room temperature for 5 minutes to obtain the catalyst for use.

3. Ethylene Trimerization 500 ml autoclave is heated and vacuumed for 2 hours. After $N_2$ exchange for several times, ethylene is introduced therein. The temperature is reduced to predetermined temperature. The dehydrated cyclohexane (200 ml) and the catalyst as obtained above are added. Oligomerization is carried out at 20° C. under the pressure of 7.0 MPa. After 20 minutes, the temperature is reduced by ice bath, the pressure is relieved, and the reaction is terminated by 10 wt % acidified alcohol. The results are listed in appended Table 1.

Example 3

1. Preparation of (diphenyl)phosphonitryl(fluorenyl)phosphine(diphenyl) ligand (1) Preparation of N,N-diisopropyldichlorophosphoamide
The process is the same as that in Example 1.
(2) Preparation of Grignard Reagent Phenylmagnesium Bromide
The process is the same as that in Example 1.
(3) Preparation of Diphenyl Phosphorus Chloride
The process is the same as that in Example 1.
(4) Preparation of (diphenyl)phosphonitryl(fluorenyl)phosphine(diphenyl)

To a 100 ml reactor with $N_2$ sufficient exchange, the dehydrated dichlormethane (20 ml), triethylamine (3.75 ml) and diphenyl phosphorus chloride (1.326 ml, 7.2 mmol) are added under stirring. The temperature is reduced to 0° C. The fluorenamine (0.652 g, 3.6 mmol) is added slowly. The reaction is carried out under stirring for 30 minutes and then raised to room temperature to continue for 12 hours. The product (0.48 g, 24.3%) is finally obtained after filtrating and drying.

2. Preparation of Catalyst

To a 100 ml reactor with $N_2$ sufficient exchange, the dehydrated cyclohexane (10 ml), tripropylaluminium (10 ml), $SiO_2$ (0.1 mmol), (diphenyl)phosphonitryl(fluorenyl)phosphine(diphenyl) (35 mg), $Cr(acac)_3$ (12 mg) and 1,2-dimethoxyethane (0.4 ml, 0.031 mmol) are added. The reaction is undergone at room temperature for 5 minutes to obtain the catalyst for use.

3. Ethylene Trimerization 500 ml autoclave is heated and vacuumed for 2 hours. After $N_2$ exchange for several times, ethylene is introduced therein. The temperature is reduced to predetermined temperature. The dehydrated benzene (200 ml) and the catalyst as obtained above are added. Oligomerization is carried out at 30° C. under the pressure of 3.0 MPa. After 20 minutes, the temperature is reduced by ice bath, the pressure is relieved, and the reaction is terminated by 10 wt % acidified alcohol. The results are listed in appended Table 1.

Example 4

1. Preparation of 1,4-bis(N(P(phenyl)$_2$)$_2$)-benzene ligand (1) Preparation of N,N-diisopropyldichlorophosphoamide
The process is the same as that in Example 1.
(2) Preparation of Grignard Reagent Phenylmagnesium Bromide
The process is the same as that in Example 1.
(3) Preparation of Diphenyl Phosphorus Chloride
The process is the same as that in Example 1.
(4) Preparation of 1,4-bis(N(P(phenyl)$_2$)$_2$)-benzene
To a 100 ml reactor with $N_2$ sufficient exchange, the dehydrated dichlormethane (20 ml), triethylamine (3.75 ml) and diphenyl phosphorus chloride (1.326 ml, 7.2 mmol) are added under stirring. The temperature is reduced to 0° C. The 1,4-phenylenediamine (0.19 g, 1.8 mmol) is added slowly. The reaction is carried out under stirring for 30 minutes and then raised to room temperature to continue for 12 hours. The product (0.8 g, 52.3%) is finally obtained after filtrating and drying.

2. Preparation of Catalyst

To a 100 ml reactor with $N_2$ sufficient exchange, the dehydrated cyclohexane (10 ml), tributylaluminium solution (7 ml), $SiO_2$ (0.3 mmol), 1,4-bis(N(P(phenyl)$_2$)$_2$)-benzene (27 mg), chromium 2-ethylhexanoate (10 mg) and 1,2-dichlorethane (0.13 mmol) are added. The reaction is undergone at room temperature for 10 minutes to obtain the catalyst for use.

3. Ethylene Trimerization 500 ml autoclave is heated and vacuumed for 2 hours. After $N_2$ exchange for several times, ethylene is introduced therein. The temperature is reduced to predetermined temperature. The dehydrated heptane (200 ml) and the catalyst as obtained above are added. Oligomerization is carried out at 100° C. under the pressure of 7.0 MPa. After 10 minutes, the temperature is reduced by ice bath, the pressure is relieved, and the reaction is terminated by 10 wt % acidified alcohol. The results are listed in appended Table 1.

Example 5

1. Preparation of (diphenyl)phosphonitryl(isopropyl)phosphine(diphenyl) ligand (1) Preparation of N,N-diisopropyldichlorophosphoamide
The process is the same as that in Example 1.
(2) Preparation of Grignard Reagent Phenylmagnesium Bromide
The process is the same as that in Example 1.
(3) Preparation of Diphenyl Phosphorus Chloride
The process is the same as that in Example 1.
(4) Preparation of (diphenyl)phosphonitryl(isopropyl)phosphine(diphenyl)
The process is the same as that in Example 1.

2. Preparation of Catalyst

To a 100 ml reactor with $N_2$ sufficient exchange, the dehydrated xylene (10 ml), $SiO_2$ (0.09 mmol), triisobutylaluminium (10 ml), (diphenyl)phosphonitryl(isopropyl)phosphine(diphenyl) (29 mg), $CrCl_3 \cdot (THF)_3$ (12 mg), and 1,4-dichlorbenzene (0.069 mmol) are added under stirring. The reaction is undergone at room temperature for 5 minutes to obtain the catalyst for use.

3. Ethylene Trimerization 500 ml autoclave is heated and vacuumed for 2 hours. After $N_2$ exchange for several times, ethylene is introduced therein. The temperature is reduced to predetermined temperature. The dehydrated xylene (200 ml) and the catalyst as obtained above are added. Oligomerization is carried out at 20° C. under the pressure of 5.5 MPa. After 60 minutes, the temperature is reduced by ice bath, the pressure is relieved, and the reaction is terminated by 10 wt % acidified alcohol. The results are listed in appended Table 1.

PRACTICAL APPLICABILITY

This catalyst is used for catalyzing the synthesis of 1-hexene from ethylene trimerization in an inert solvent. The catalyst is prepared by mixing the components of (a)-(e) in a suitable ratio in an ethylene trimerization conventional apparatus in situ under ethylene pressure. And ethylene is introduced into the apparatus continuously so as to get in contact with the catalyst sufficiently, then the ethylene trimerization is performed at the temperature of 30-150° C. under the pressure of 0.5-10.0 MPa for 0.1-4 hours. The catalyst is used to prepare 1-hexene by ethylene trimerization. The catalyst has high catalytic activity and high 1-hexene selectivity. The by-product polyethylene does not stick to the apparatus. The results are listed in appended Table 1.

Appended TABLE 1

|  | Example 1 | Example 2 | Example 3 | Example 4 | Example 5 |
|---|---|---|---|---|---|
| catalytic activity (g oligomer/ mol Cr · h) _ $10^7$ | 5.8 | 4.1 | 6.4 | 5.1 | 1.6 |
| 1-butene selectivity (wt %) | 0.3 | 0.4 | 0.8 | 0.4 | 0.9 |
| 1-hexene selectivity (wt %) | 95.1 | 95.2 | 95.2 | 96.3 | 97.2 |
| polymer (wt %) | 0.02 | 0.05 | 0.04 | 0.07 | 0.02 |

What is claimed is:

1. A catalyst for synthesizing 1-hexene from ethylene trimerization, comprising:
(1) compound (a) containing P and N, with formula:

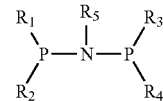

wherein $R_1$, $R_2$, $R_3$ and $R_4$ independently are selected from the group consisting of phenyl, benzyl and naphthyl, and $R_5$ is selected from the group consisting of isopropyl, butyl, cyclopropyl, cyclopentyl, cyclohexyl, and fluorenyl;

(2) electron donor (b), which is 1,4-dichlorobenzene, 1,1,2-trichloroethane, 1,1,2,2-tetrachloroethane, 1,1,2,2-tetrabromoethane, 1,2-dichlorethane, 1,2-dimethoxyethane, chlorobenzene, 1,2-dichlorobenzene, 1,3-dichlorobenzene, and/or 1,4-dichlorobenzene;

(3) Cr compound (c), which is chromium isooctoate, chromium chloride tetrahydrofuran, chromium 2-ethylhexanoate, and/or chromium acetylacetonate;

(4) carrier (d), which is $SiO_2$; and (5) accelerator (e), which is trimethylaluminium, triethylaluminium, tripropyl aluminium, tributylaluminium and/or triisobutylaluminium;

wherein a molar ratio of (a), (b), (c), (d) and (e) is 1-80:1-70:1:1-8:100-4000.

2. The catalyst of claim 1, wherein in compound (a) $R_1$, $R_2$, $R_3$ and $R_4$ are phenyl and $R_5$ is cyclopropyl, cyclopentyl, fluorenyl, or isopropyl; electron donor (b) is 1,1,2,2-tetrachloroethane, 1,1,2,2-tetrabromoethane, 1,2-dimethoxyethane, 1,2-dichlorethane or 1,4-dichlorobenzene; Cr compound (c) is chromium isooctoate, chromium chloride tetrahydrofuran, chromium 2-ethylhexanoate, or chromium acetylacetonate; carrier (d) is $SiO_2$; and accelerator (e) is triethylaluminium, trimethylaluminum, tripropylaluminium, tributylaluminium, or triisobutylaluminium.

3. A method for synthesizing 1-hexene from ethylene trimerization, comprising:

preparing the catalyst of claim 1 by mixing the components of (a)-(e) in the molar ratio in an ethylene trimerization apparatus in situ under ethylene pressure in an inert solvent;

introducing ethylene into the apparatus continuously such that the ethylene substantially contacts the catalyst; and performing the ethylene trimerization at a temperature of about 20° C. to about 150° C. under a pressure of about 0.5 MPa to about 10 Mpa for about 0.1 hour to about 4 hours, thereby synthesizing the 1-hexene.

4. The method of claim 3, wherein the inert solvent is selected from the group consisting of an alkane, an aromatic hydrocarbon, a halohydrocarbon, an alkene, and an ionic liquid.

5. The method of claim 4, wherein the alkane is n-heptane, methyl cyclohexane, or cyclohexane.

6. The method of claim 4, wherein the aromatic hydrocarbon is benzene, toluene, xylene, or isopropylbenzene.

7. The method of claim 4, wherein the alkene is 1-hexene or 1-octylene.

8. The method of claim 3, wherein the temperature is about 20° C. to about 90° C.

9. The method of claim 3, wherein the pressure is about 1 MPa to about 10 Mpa.

10. The method of claim 3, wherein the pressure is about 2 MPa to about 6 Mpa.

11. The method of claim 3, wherein the ethylene trimerization is performed for about 0.3 hours to about 1 hour.

12. The method of claim 3, wherein the ethylene trimerization is performed for about 0.5 hours to about 0.7 hours.

\* \* \* \* \*